United States Patent [19]

Schreck

[11] 4,399,305

[45] Aug. 16, 1983

[54] PRODUCTION OF ETHYLENE BY THE PYROLYSIS OF ETHYL ACETATE

[75] Inventor: David J. Schreck, Cross Lanes, W. Va.

[73] Assignee: Union Carbide Corporation, Danbury, Conn.

[21] Appl. No.: 435,095

[22] Filed: Oct. 18, 1982

[51] Int. Cl.³ .................. C07C 53/08; C07C 1/00
[52] U.S. Cl. .................................. 562/607; 585/639
[58] Field of Search ............... 585/639, 638; 562/607

[56] References Cited

U.S. PATENT DOCUMENTS 1,770,734 7/1930 Engelhardt et al.
2,286,407 6/1942 Halbig ................................ 260/542
2,304,872 12/1942 Bachman et al. ................... 260/541
2,542,488 2/1951 Dinwiddie ........................... 260/282
3,068,305 12/1962 Heisler et al. ...................... 260/682
4,065,512 12/1977 Cares .................................. 260/641
4,232,177 11/1980 Smith, Jr. ........................... 585/639
4,270,015 5/1981 Knifton ............................... 585/639

FOREIGN PATENT DOCUMENTS 546255 9/1957 Canada ............................... 562/607

Primary Examiner—Delbert E. Gantz
Assistant Examiner—Cynthia A. Prezlock
Attorney, Agent, or Firm—Bernard Francis Crowe

[57] ABSTRACT

High purity ethylene is prepared by contacting ethyl acetate with a perfluorosulfonic acid resin catalyst at 150°–250° C.

4 Claims, No Drawings

PRODUCTION OF ETHYLENE BY THE PYROLYSIS OF ETHYL ACETATE

DESCRIPTION

BACKGROUND OF THE INVENTION

This invention pertains to the production of ethylene and more particularly to the pyrolysis of ethyl acetate to achieve this end.

BACKGROUND ART

Production of ethylene on a large scale has been practiced in the United States for more than fifty years. Ethylene is the starting material for a myriad of products and is the largest volume organic chemical made in this country. For many years it has been made by thermally cracking natural gas liquids, chiefly ethane and propane. Recently, the supplies of such liquids have not been adequate to provide the demand for ethylene. Consequently, manufacture from naphtha (a fraction from petroleum refining) by a steam cracking process has been used to make a substantial amount of the ethylene required by industry.

It has been predicted that the demand for ethylene as a starting material for polymerization to polyethylene as well as for the synthesis of ethylene glycol, styrene and other chemicals will continue to grow. The supply of natural gas liquids has already reached a peak and is declining. Petroleum production in the United States is falling off and foreign supplies are getting more costly and less available. With the prospect of ethylene becoming more expensive and harder to get, various means of supplementing the present supply and providing even more for the future have been, and are being, considered.

One such route to the production of ethylene is the conversion of synthesis gas, a mixture of hydrogen and carbon monoxide, to ethylene. One way that this is accomplished is by passing the synthesis gas in the vapor phase over a bed of catalyst composed of specially treated molecular sieves. This reaction produces a rather wide range of products. The efficiency of the conversion of synthesis gas to ethylene is in the range of 30%. Thus far, the low selectivity has prevented this route from being considered as a commercial process for at least two or three decades.

Another method of making ethylene is by the dehydration of ethanol. Ethanol is made synthetically at present by the reverse of this reaction, that is by the addition of water to the olefinic double bond of ethylene. Another source of ethanol is the fermentation of natural products such as carbohydrates from grain or sugar. Fermentation as a route to ethanol is now practiced on a large scale and a number of additional plants are being constructed to make alcohol for use as an automobile fuel component. Consequently, large quantities of ethanol from regenerable raw materials are potentially available for dehydration to ethylene. The drawback to this is that the reaction is not clean cut. Primary alcohols are relatively difficult to dehydrate to olefins and substantial amounts of ethers are formed as by-products. Thus far, no one has practiced dehydration of ethanol on a large scale in this country.

The pyrolysis of esters to make olefins and acids is an old reaction and in fact the pyrolysis of ethyl acetate was first performed about fifty years ago. Various investigators have published accounts of modifications of this basic reaction and in general it was assumed that the gas produced was ethylene of acceptable purity. Recent studies have shown that this was not the case.

A recent reference on this reaction can be found in U.S. Pat. No. 4,270,015. This patent covers an overall process in which synthesis gas was reacted with an aliphatic acid or anhydride to produce esters which were then decomposed to make olefins and acids. The reaction to make the esters was conducted with a ruthenium catalyst at fairly high pressures. The pyrolysis of esters produced by this process and particularly the ethyl esters was conducted in a quartz reactor packed with glass helices at a temperature of 400°–450° C. The reaction rate was quite slow and based on the data given in the examples the conversion was only about 30–40%. A complete analysis of the gaseous portion of the product was not given but in at least two instances it was shown to contain relatively high amounts of ethane.

U.S. Pat. No. 3,068,035 discloses a process for preparing an olefin, isobutylene, by the decomposition of t-butyl esters using temperatures between 90°–225° F. and a catalyst. Sulfuric acid is described as the preferred catalyst.

The decomposition of esters at temperatures above 350° C. in the presence of a catalyst-containing copper and boric acid is disclosed in U.S. Pat. No. 2,304,872. Decomposition of ethyl acetate to yield acetic acid and ethylene is disclosed. The purity of the ethylene is not revealed.

U.S. Pat. No. 2,286,407 discloses a process wherein an ester of formic acid is split up into olefins and formic acid by heat (108° C.). The decomposition is accelerated by the use of catalysts such as acids.

It is therefore an object of this invention to provide a method for pyrolyzing ethyl acetate to a high purity ethylene.

It is another object of this invention to provide a method for the pyrolysis of ethyl acetate to high purity ethylene catalytically at high productivities.

Other objects will become apparent to those skilled in the art upon the further reading of the specification.

DISCLOSURE OF THE INVENTION

A process for making ethylene in high purity has been found which comprises contacting ethyl acetate at a temperature of about 150° C. to about 250° C. with a catalytic amount of a perfluorosulfonic acid resin catalyst, which is a copolymer of tetrafluoroethylene and a sulfonyl fluoride vinyl ether, at a contact time of at least about one second and continuously removing ethylene and acetic acid from the reaction zone.

Although temperatures of about 150° C. to about 250° C. can be used, it is preferred to use a temperature of about 160° to 225° C.

Pressure is not narrowly critical. Super-atmospheric pressures as well as sub-atmospheric and normal pressures can be used in the practice of this invention. For economic reasons it is preferred to use atmospheric or slightly super-atmospheric pressures.

The ethyl ester used as the starting material in the reaction of this invention is not limited to any single source. For instance, by-product esters from the liquid-phase oxidation of low-molecular weight hydrocarbons, such as the oxidation of butane, ethyl acetate from the esterification of acetic acid with ethanol produced by fermentation or esters made by reaction of synthesis gas with acids using catalysts from various metals can all be used for this reaction.

The perfluorosulfonic acid resin used as catalyst in this invention is commercially available under the trademark Nafion from the duPont de Nemours Company at Wilmington, Delaware. Suitable variations of these resins are described in U.S. Pat. No. 4,065,512 and in duPont "Innovation", volume 4, number 3, spring 1973.

The term "catalytic amount of perfluorosulfonic acid resin" is meant to mean concentrations based on the total reaction mixture of about 0.001 percent to about 50 percent by weight.

It is surprising to find that the perfluorosulfonic acid resins were as active as conventional strong acids such as sulfuric acid or phosphoric acid. In addition, the Nafion catalyst resins were extremely resilient and did not deteriorate in physical form to a powder during use as did other solid resins such as ion exchange resins. No signs of wear or tear have been observed in the these catalysts after many hours of use making ethylene and acetic acid. Furthermore, because of this great durability, the Nafion catalysts are ideally suited for use as catalysts in tubular type reactions, fluidized bed-type reactors, as well as reactors of various geometric shapes.

As polymer-supported catalysts, Nafion is also well suited for use in packed bed reactors.

The invention is further explained in the examples which follow. All parts and percentages are by weight unless otherwise specified.

Control A—Thermal Pyrolysis in Copper Reaction System

The equipment used was a graduated feed tank, a Lapp metering pump, a ¼" OD heated copper line as a pre-heater, a ½" OD concentric copper tubing 26 inches long as a reactor with a ¼" OD thermowell, an insulated hinged heater 12" long into which the reactor was fitted, a water-cooled condenser, product receiver, gas exit line connected to a wet test meter and a gas sample line. The volume of the reactor with thermowell was 20 ml.

The preheater temperature was maintained at 413°–415° C. and the hottest portion of the reactor at about 650° C. Ethyl acetate was fed at the rate of 200 ml per hour. This gave a contact time of approximately 1.6 seconds in the heated zone. The effluent strain was cooled in the condenser and the liquid portion collected and weighed. The gas stream was measured and samples were obtained periodically and analyzed.

The liquid was almost pure acetic acid with a trace of water. The gas stream contained:

| Component | Weight Percent |
|---|---|
| Ethylene | 96.16 |
| Methane | 1.226 |
| Carbon Dioxide | 1.687 |
| Ethane | 0.471 |
| Carbon Monoxide | 0.453 |

The conversion of ethyl acetate was approximately quantitative. As may be seen, the gas stream contained 4,500 parts per million of carbon monoxide, making it unacceptable for many of the accepted chemical uses for ethylene. Carbon monoxide is a poison for many of the catalysts used in ethylene polymerization reactions.

Control B

The operation was similar to that of Control A except that a stainless steel tube was used instead of copper. Ethyl acetate was fed at the rate of 400 ml/hour and the temperature in the pyrolysis zone ranged between 495°–600° C. The gas portion of the product contained:

| Component | Weight Percent |
|---|---|
| Ethylene | 79.89 |
| Ethane | 0.78 |
| Carbon Dioxide | 11.14 |
| Methane | 2.0 |
| Carbon Monoxide | 6.31 |

The conversion of ethyl acetate to ethylene was 73 percent. As may be seen the very high concentration of carbon monoxide, viz., 6.3 percent, would make the ethylene prepared in this manner totally unuseable.

Control C

The following experiment was run in a quartz reactor packed with glass helices according to the procedure of U.S. Pat. No. 4,270,015.

Pyrolysis of Ethyl Acetate

The equipment comprised a 30" long by 1" ID quartz tube, glass helices for packing the tube, a 12" hinged heater, a Lapp metering pump, a graduated feed tank, ⅛" stainless steel feed line, heating tape, helium source, quartz thermowell, thermocouple wire, water cooled condenser (glass), glass receiver, dry ice cold traps, gas sample bottles, and a wet test meter. The feed rates of ethyl acetate diluted with helium were 1.2435 moles per hour or 110 cc per minute.

The physical conditions were a reactor temperature of 700° C. and atmospheric pressure.

The procedure used was to feed ethyl acetate with a Lapp metering pump through a ⅛" stainless steel feed line preheated to 170° C. to vaporize the feed before entering the reactor. The vaporized ethyl acetate was carried by a 60 cc per minute flow of helium through the 30"×1" inch ID quartz tube reactor. The quartz tube was packed with glass helices and heated by means of a 12" long hinged heater. The remaining length of the tube was heated with heating tape to prevent rapid cooling. The reactor temperature was monitored using a thermocouple housed in a quartz thermowell which extended through the length of the reactor which allowed the thermocouple to be placed at any position throughout the reaction.

The effluent gas passed through the tube to a glass water cooled condenser where the condensate was collected in a glass receiver which was vented to dry ice cold traps through gas sample bottles to a wet test meter which recorded the off gas in cubic feet per hour.

The gas portion was analyzed and it contained:

| Component | Weight Percent |
|---|---|
| Ethylene | 96.5 |
| Carbon Dioxide | 1.52 |
| Methane | 1.09 |
| Ethane | 0.5422 |
| Carbon Monoxide | 0.3349 |

The conversion of ethyl acetate was quantitative. As may be seen, the carbon monoxide content was 3,349 parts per million. This is still too high for the ethylene to be acceptable for chemical use.

EXAMPLE 1

The following experiment demonstrates the instant invention using a Nafion catalyst.

A 30" long by 1" ID quartz reactor tube with male ball joint fittings at each end, size 28/15. The tube was packed with a 12" oven zone of Nafion tubing with glass beads as the support filling the remaining length of the tube. A Lapp meter pump, ⅛" stainless steel feed line, heat wrapped, quartz thermowell, 12" hinged heaters, glass water cooled condensor, glass collection reservoir, wet ice cold traps, gas sampling bottles, and a wet test meter completed the equipment.

The hottest portion of the reactor was held at 185° C. while ethyl acetate was fed through the reactor at a rate of 116 ml per hour. The conversion of ethyl acetate was 19.35%. The gaseous portion of the product was analyzed and found to contain:

| Component | Weight Percent |
| --- | --- |
| Ethylene | 100.0 |
| Carbon Monoxide | none detected |
| Carbon Dioxide | none detected |
| Methane | none detected |
| Ethane | none detected |

This experiment demonstrates that ethylene made in this fashion is virtually free of carbon monoxide plus inert materials such as methane, carbon dioxide and ethane which would detract from its use if present.

Although the invention has been described in its preferred forms with a certain degree of particularity, it is understood that the present disclosure has been made only by way of example and that numerous changes can be made without departing from the spirit and scope of the invention.

I claim:

1. Process for making ethylene in high purity which comprises contacting ethyl acetate at a temperature of 150° C. to about 250° C. with a catalytic amount of a perfluorosulfonic acid resin catalyst, which is a copolymer of tetrafluoroethylene and a sulfonyl fluoride vinyl ether, at a contact time of at least about 1 second and continuously removing ethylene and acetic acid.

2. Process claimed in claim 1 wherein the ethyl acetate is passed through a tubular reactor packed with solid catalyst thereby facilitating control of the contact time.

3. Process claimed in claim 1 wherein the temperature is maintained in the range from about 150° C. to 250° C.

4. Process claimed in claim 2 wherein the tubular reactor is fabricated from quartz.

* * * * *